United States Patent [19]

Creekmore

[11] Patent Number: 4,529,382
[45] Date of Patent: Jul. 16, 1985

[54] LINGUAL ORTHODONTIC APPLIANCE SYSTEM FOR EDGEWISE THERAPY

[76] Inventor: Thomas D. Creekmore, 1620 Fountainview, Houston, Tex. 77057

[21] Appl. No.: 369,932

[22] Filed: Apr. 19, 1982

[51] Int. Cl.³ .............................................. A61C 7/00
[52] U.S. Cl. ........................................ 433/9; 433/16
[58] Field of Search .................... 433/16, 9, 15, 17, 14

[56] References Cited

U.S. PATENT DOCUMENTS

| | | | |
|---|---|---|---|
| 1,481,861 | 1/1924 | Eaton | 433/17 |
| 3,435,527 | 4/1969 | Kesling | 433/16 |
| 3,626,593 | 12/1971 | Ridgeway | 433/11 |
| 3,765,091 | 10/1973 | Northcutt | 433/9 |
| 4,337,037 | 6/1982 | Kurz | 433/8 |

FOREIGN PATENT DOCUMENTS 1428673 3/1976 United Kingdom ................. 433/15

*Primary Examiner*—Robert Peshock
*Attorney, Agent, or Firm*—Gunn, Lee & Jackson

[57] ABSTRACT

An orthodontic bracket system for edgewise orthodontic therapy which is adapted for attachment to the lingual surface portions of a patient's teeth. The lingual orthodontic bracket system of this invention is designed to permit occlusal and mesial insertion of an edgewise archwire into precision archwire slots that are defined by the respective brackets of incisors, cuspids, bicuspids and molars. At least some of the lingual orthodontic brackets incorporate fulcrum controlled twin tie wing systems to permit efficient controlled rotation of the teeth as well as archwire tipping and torque activities. The lingual bracket system of this invention also incorporates a molar tube that is designed for mesio-occlusal insertion of the end portion of the edgewise archwire and also permits pivoting or rotation of the archwire about the molar tube structure so as to bring the archform portion thereof occlusally into properly seated relation with respect to the archwire slots of other brackets.

15 Claims, 17 Drawing Figures

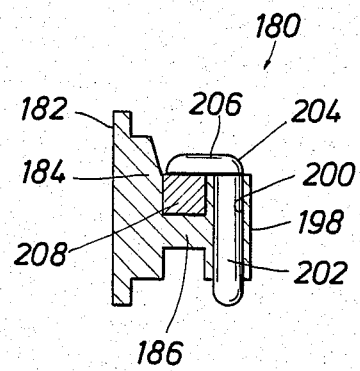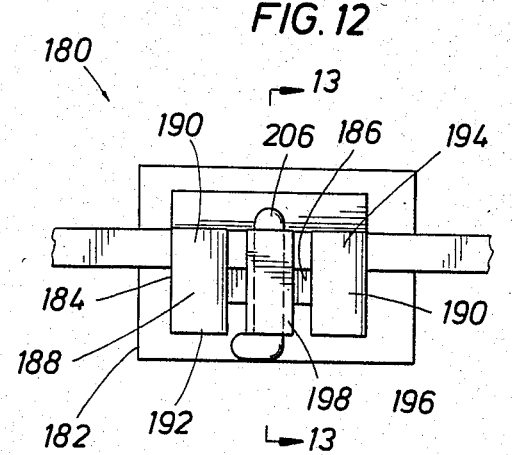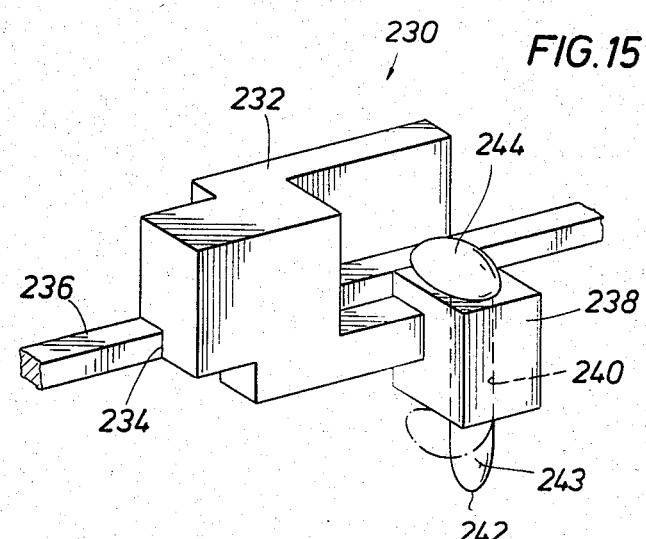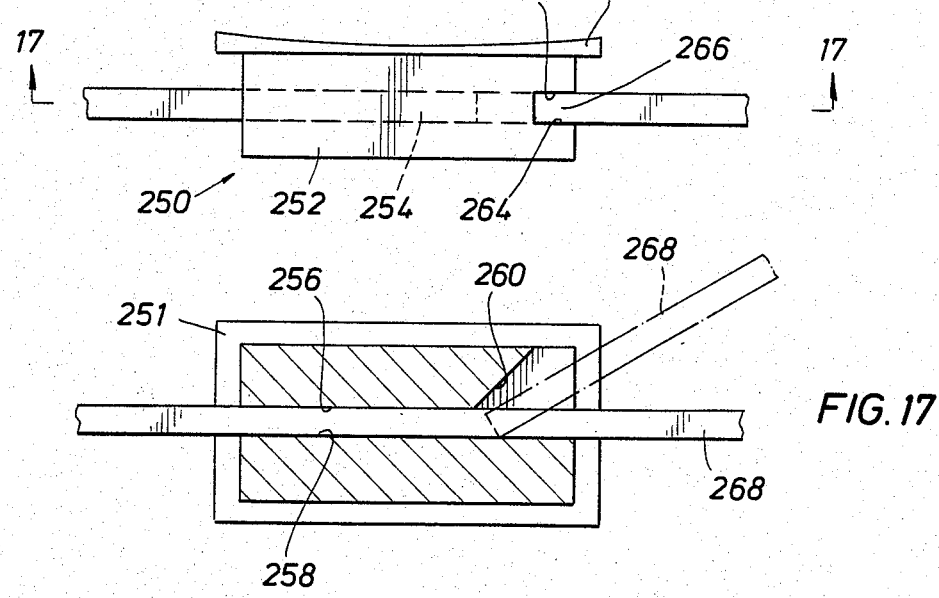

LINGUAL ORTHODONTIC APPLIANCE SYSTEM FOR EDGEWISE THERAPY

FIELD OF THE INVENTION

This invention relates generally to orthodontic brackets which are utilized by orthodontists to accomplish accurate movement and positioning of the teeth of a patient. More specifically, the present invention concerns the provision of a lingual orthodontic bracket system which may be utilized to permit the labial and buccal surfaces of the teeth to be free of orthodontic applicances to thus retain a pleasing appearance during the period of orthodontic therapy. Even further, this invention concerns the provision of a lingual orthodontic bracket system which permits orthodontists to impart forces directly to the lingual surfaces of a patient's teeth in order to accomplish desirable tooth movement.

BACKGROUND OF THE INVENTION

Although a number of differing orthodontic techniques exist, the majority of orthodontists in practice in the United States, at the present time, utilize one of two basic techniques of orthodontic therapy in their treatment of patients. These basic techniques are the "light-wire" technique and the "edgewise" technique. Light-wire appliances were first designed and presented to the profession by an Australian orthodontist, R. P. Begg, who introduced the idea of differential force control. Since some types of tooth movements evoke more tissue resistance than others, and some movements occur faster than others, Begg reasoned that by selectively choosing the movements required and relating the reciprocal reactions properly, tooth movement might be accomplished in orderly manner. The Begg light-wire technique is characterized by a number of significant features. Brackets are fixed to all of the teeth of the patient anterior to and including the first molars. Archwires are round in cross-section and provide archform and leveling of the teeth. Archwires are loosely pinned to the bracket and are not ligated. The Begg brackets provide a single point contact with the archwire to minimize friction and permit the teeth to slide, rotate, tip and torque freely. Tip, torque and rotation are accomplished by auxiliaries and not by the active fit between the archwire and bracket as in the edgewise technique. Extra oral anchorage is not used. Reciprocal anchorage is provided for by selectively utilizing teeth posterior to extraction sites to retract teeth anterior to the extraction sites with intra and inter maxillary elastics. The light-wire appliances are now several and varied from the original design, although all employ sophisticated concepts in theories of tooth movement and anchorage control. Standard light-wire therapy does not utilize extra-oral traction, frequently involves extraction of teeth and typically employs more auxiliaries than conventional edgewise therapy.

The most widely utilized orthodontic therapy technique in this country, and the technique to which this invention is directed, is the "edgewise" technique, which was brought to the industry by Dr. Edward H. Angle. It should be understood, however, that this invention is also applicable to other orthodontic techniques such as the multi-phase and twin wire techniques, for example. In the beginning stages of edgewise therapy, archwires of circular cross-sectional configuration are employed. The greater flexibility of the round wire used in initial edgewise therapy permits greater range of movement of malposed teeth with less force to the teeth. For secondary and finishing therapy, the edgewise technique typically incorporates a multi-banded precision appliance consisting of a labial archwire of rectangular cross-section configuration that is ordinarily of greater dimension at the sides than at the edges thereof. The archwire is fitted and ligated with metal ligature wire, or ligature elastics, or any other suitable form of mechanical retention, into precision mating horizontal archwire slots that are formed in brackets on all of the permanent teeth including first molars and frequently second molars. The archwire terminates in buccal tubes each having a rectangular passage through which the end portions of the rectangular archwire extend. The archwire, which may be composed of stainless steel or precious alloy, is typically positioned with its narrow dimension or edge lying against the labial and buccal surfaces of the teeth. This feature gives the technique its name "edgewise." The edgewise technique makes control possible in all directions and any individual tooth may be moved simultaneously in three directions; for example, an incisor may be moved lingually, distally and rotated around its long axis with one adjustment of the archwire. The rectangular cross-sectional configuration of the edgewise archwire permits it to be twisted to a desired extent and, being of spring-like nature, the twisting forces will be applied through the archwire to the teeth, thereby inducing a torquing movement of the teeth as the archwire becomes untwisted and returns to its normal configuration. The brackets are precision milled to define archwire slots of rectangular shape so that the orthodontist can select precision milled archwires to fit as precisely as desired. Tip, torque and rotation are accomplished by the fit between the archwire and the bracket. Extra oral anchorage may or may not be used as desired. Reciprocal anchorage can be provided by extraction of teeth and selectively utilizing teeth posterior to extraction sites to retract teeth anterior to the extraction sites with intra and inter maxillary elastics and/or closing loop archwires. This invention is generally directed to the edgewise technique and concerns an orthodontic appliance system that integrates specific advantages that are afforded by edgewise appliances with both single and twin ligating tie wings.

As mentioned above, conventional edgewise therapy is typically accomplished by means of a labial archwire that is received by precision archwire slots formed by orthodontic brackets that are positioned at the labial surfaces of a patient's teeth. In many cases, undesirable psychological phenomena occurs since the otherwise pleasant appearance of a patient's teeth might be considered unpleasant, especially by the patient, because of the presence of orthodontic appliances on the labial and buccal surfaces of the patient's teeth. Suppliers of orthodontic brackets and systems, to provide more esthetically pleasing appliances, have in some cases eliminated metal bands that encircle the teeth and have developed brackets that are adapted for direct bonding to the enamel surface of the teeth. Still, with the archwire present at the labial and buccal surfaces of the patient's teeth, it is not possible to provide the patient with an orthodontic appliance system that presents the teeth in their normal appearance. Further, by positioning orthodontic brackets on the labial and buccal surfaces of the patient's teeth, the orthodontic brackets frequently cause tissue irritation with the lip and mouth tissues of the patient. Moreover, the mere presence of orthodontic brackets between the teeth and lips or cheeks can intefere to some extent with muscle tone and develop undesirable speech characteristics. In some cases, a patient's teeth may tend to decalcify or become permanently discolored in the area covered by or adjacent to metal bands. Also, in many cases, the orthodontic appliances interfere with efficient oral hygiene and caries can develop on tooth surfaces that cannot be properly cleaned. Consequently, when the appliances are removed from the patient's teeth, the otherwise pleasant appearance of properly occluding teeth can be marred by irregular surfaces, band lines of discoloration and fissures that can be developed in the enamel. By locating the appliances on the lingual surfaces of the patient's teeth, the labial surface will remain clear of obstructions that otherwise would interfere with efficient oral hygiene. It is desirable, therefore, to provide for lingual edgewise orthodontic therapy because of the effective nature thereof and to allow the labial surfaces of the teeth of the patient to remain unobstructed to permit efficient cleaning thereof and to provide the patient with a pleasant facial appearance during the period of orthodontic therapy. It is also desirable to provide lingual edgewise orthodontic therapy without subjecting the patient to the presence of brackets and archwires between the teeth and lip and cheek surfaces.

In some cases, it is desirable that the orthodontist be capable of applying tooth movement forces to the lingual surfaces of a patient's teeth. With conventional edgewise therapy, forces are typically applied through brackets that are positioned only at the labial and buccal surfaces. It is desirable, therefore, to provide orthodontic brackets that permit edgewise therapy through location of orthodontic brackets at the lingual surfaces of the patient's teeth.

Single brackets for edgewise therapy typically incorporate a base structure which is formed to define a precision active archwire slot which receives the rectangular edgewise archwire therein. Single brackets also incorporate a pair of tie wings that extend from the base and are positioned on opposite sides of the precision archwire slot. These tie wings are typically centered with respect to the bracket structure and are therefore intended to be positioned in substantially centered mesio-distal relation with the facial surface of the tooth to which the bracket is secured. A ligature wire or elastic is looped over each of the tie wings and is passed over the archwire, thus securing the archwire firmly in its precision slot.

Single brackets provide maximum efficiency in the application of tipping and torquing movements to teeth but are minimally efficient in rotational control. Initially, rotational control was accomplished by soldering or welding eyelets at the extreme mesial or distal of the band attached to the tooth. The orthodontist could ligate the eyelet to the archwire, pulling that surface closer to the archwire and causing the tooth to rotate about the centrally located bracket. This is a cumbersome and inefficient method of rotational control.

Subsequently, fixed or flexible rotation levers, projecting mesially and distally, were added to the centrally located single bracket. Thus, a rotated tooth would have the rotation wing projecting more facially than the bracket. The archwire would touch the rotation wing and, as the wire is ligated into the bracket, cause the tooth to rotate about the bracket. The rotation lever is adjustable to project more or less to the facial as desired. This permits the orthodontist to select the amount of rotation desired by adjusting the rotation lever rather than adjusting the archwire.

The disadvantage of the rotation lever is evident in the initial stages of treatment. The archwire will not touch the rotation lever if a tooth is tipped and rotated severely and will prevent either action from occurring unless the archwire is adjusted to strike the rotation lever when ligated. Thus, initial archwire insertion can be inefficient and require more expertise to ligate.

Twin brackets were introduced to alleviate the inefficient rotation effectiveness of the single bracket. Instead of one centrally located bracket, two brackets were placed at the mesial and distal portions of the tooth. Thus, when each bracket is ligated to the archwire, the facial surface will align itself with the archwire, rotating the tooth.

One of the principles of rotation in orthodontics is over-correction of the original problem to compensate for the rebound or relapse tendency. This is especially indicated for rotated teeth. Twin brackets do not have the capacity to over-rotate within themselves. For over-rotation with twin brackets, the archwire has to be bent or some auxilliary must be added to force the mesial or distal portion of the bracket away from the archwire. Further, single edgewise brackets, without rotation levers, are also locking in over-rotation control capability which will be discussed in more detail hereinbelow.

One of the more important advantages of single brackets is the advantage that is afforded by the active length of archwire existing between the points of connection to adjacent brackets. This active archwire length is known in the industry as "interbracket width". Since the connecting point between adjacent single brackets is established at substantially the center of the adjacent teeth, the archwire length, and thus the interbracket width, extends to points near the centers of adjacent teeth. The lengthy archwire span that exists between single brackets allows lower magnitude forces to be applied to the teeth over longer periods of time as compared to circumstances where the interbracket width is limited and the active archwire span is short. The long span of archwire may be twisted much further without causing permanent yielding or deformation of the metal of the archwire. Where the archwire between brackets is of limited length, which is typical where twin brackets are employed with the edgewise technique, application of large magnitude forces to the teeth can occur with only minimal twisting or other deformation of the archwire. Thus, after limited movement of the teeth occurs, the forces induced by the archwire dissipate quickly, thereby requiring frequent adjustment in order to maintain optimum force application. Of course, it is evident that frequent adjustment of orthodontic appliances necessitates frequent visits by the patient for adjustment of the orthodontic appliance and is therefore disadvantageous to the patient in this regard. Such frequent adjustment also requires a significant amount of chair time in the office of the orthodontist, thereby either increasing the cost of treatment to the patient, or minimizing the commercial advantage of orthodontic treatment on the part of the orthodontist. It is desirable, therefore, to provide a system for orthodontic treatment wherein patient visits are minimized and chair time is also minimized, to the mutual benefit of both the patient and orthodontist.

Twin brackets for the edgewise technique have been employed for a considerable period of time. Twin brackets typically incorporate a pair of spaced projections that extend from or are formed by the bracket base, each projection being formed to define a precision active archwire slot segment. The spaced active archwire slot segments cooperate to define a precision archwire slot having the effect of extending the entire length of the base. Each of the projections is provided with gingival and occlusal tie wings, the tie wings terminating at the opposed side portions of the base structure. With the base structure centered in respect to the tooth being moved, the tie wings will be positioned in pairs at opposite sides of the tooth, thereby defining bracket structure with rotational control. The orthodontist may utilize ligature wires or elastic members between selected tie wings and the archwire to develop the force moments that are necessary for efficient rotational control.

One of the typical disadvantages in utilization of twin brackets is the consequent minimization of interbracket width that exists as the result of positioning the tie wings at opposed side portions of the bracket structure. Ordinarily, as explained above, minimization of interbracket width in conjunction with the edgewise therapy, suffers the disadvantage of requiring frequent patient visits and increasing chair time because of the necessity for frequent adjustment of the appliance in order to maintain the force levels within the optimum range for efficient tooth movement. It is desirable, therefore, to provide lingual edgewise therapy with twin brackets having the interbracket width of single brackets.

Another significant disadvantage in the utilization of twin brackets is that the spaces that are typically available between the tie wings of adjacent brackets leave insufficient room between the teeth for closing loops and tie-back loops. It is desirable, therefore, to provide a lingual orthodontic appliance system that affords the advantages offered by twin brackets and yet provides ample space between certain tie wings of adjacent brackets to facilitate efficient use of closing loops and tie-back loops in conjunction with edgewise orthodontic therapy.

SUMMARY OF THE INVENTION

It is a principal feature of the present invention to provide a novel lingual orthodontic bracket system which permits utilization of edgewise orthodontic therapy at the lingual portions of the teeth.

It is also a feature of this invention to provide a novel lingual orthodontic appliance system which includes structure permitting application of efficient rotational control forces to the teeth of the patient.

It is an even further feature of this invention to provide a novel lingual orthodontic appliance system which allows the labial and buccal surfaces of the patient's teeth to remain free of orthodontic appliances, thereby permitting the normal relationship of the facial tissues and teeth to remain undisturbed and to provide the patient with a pleasant oral appearance during orthodontic therapy.

Among the several features of the present invention is contemplated the provision of a novel lingual orthodontic appliance system which enables mesial-occlusal insertion of an edgewise archwire into interfitting relation with the various orthodontic brackets of the anterior teeth, the cuspids, bicuspids and molars.

It is an even further feature of the present invention to provide a lingual orthodontic appliance system incorporating a specifically designed lingual tube that permits mesial-occlusal insertion of the end portions of an archwire therein and further permits rotation of the archwire relation to the lingual tube to permit occlusal insertion of the archwire into the precision archwire slots of other brackets of the orthodontic appliance system.

It is another feature of this invention to provide a novel lingual orthodontic appliance system employing twin tie wings for effective rotational and tipping control and which also provides for maintenance of efficient interbracket spacing to permit efficient torquing movements in response to the edgewise technique.

It is also a feature of the present invention to provide a novel lingual orthodontic appliance system enabling an orthodontist to selectively utilize various combinations of rotation and over-rotation control, torque and tipping control simply through selection of various lingual edgewise brackets of single or twin form, at least some of which embody a centralized fulcrum and at least one precision active archwire slot in according with the principals of this invention.

It is an even further feature of this invention to provide a novel lingual orthodontic appliance system embodying fulcrum control and which system is of simple nature, is comparable with other orthodontic brackets from the standpoint of ease of installation and use and suffers no competitive disadvantage in comparison with other similar orthodontic bracket systems.

Briefly, the lingual orthodontic appliance system of the present invention incorporates a base structure which is adapted to be secured in immovable relation with a tooth. The base may be attached to bands that are positioned about the teeth and cemented in place or the base may be adapted for direct bonding to the tooth structure. The lingual base and bracket structure may take any one of several different forms within the spirit and scope of this invention, depending upon the teeth to which the brackets are to be secured. Regardless of the design of the particular brackets involved in lingual edgewise therapy, the archwire slots are oriented for occlusal insertion of the archwire therein. The terminal lingual attachments are designed to retain the tubular function thereof but are also of a confirguration allowing mesio-occlusal insertion of the archwire end portions therein to thus permit occlusal insertion of the arch portion of the archwire into the respective archwire slots of each of the other brackets.

To provide for efficient rotation, the lingual brackets may be in the form of twin bracket structures having a archwire relief between each of the pairs of tie wings and an intermediate fulcrum portion that defines the precision archwire slot of the bracket. Thus, twin type lingual orthodontic brackets are provided which have maximum interbracket width such as is ordinarily afforded by single brackets for maintenance of maximum active archwire length between adjacent brackets. By providing an intermediate fulcrum section with pairs of tie wings at each extremity thereof and by providing archwire relief between each of the pairs of tie wings, a twin lingual bracket is provided having efficient rotational control. Further, since the intermediate fulcrum section of the bracket is machined to form an active archwire slot, the twin lingual brackets also incorporate the efficient tipping and torquing activity ordinarily achieved by single brackets.

Lingual brackets may also be provided of the single tie wing type as desired for particular teeth of the patient. The single tie wing lingual bracket will have an archwire slot that opens toward the occlusal and wil be extended to provide tie wings for ligating and pinning. The appliance system will include lingual tube brackets which are adapted for mesio-occlusal insertion of the archwire ends into proper position therein. Each lingual tube is designed so that the archwire may be inserted in angular or in mesio-occlusal relation therewith. After having been inserted mesio-occlusally into the lingual tubes, the archwire is pivoted about pivot portions defined by the tubes to thus allow occlusal insertion of the arch portions of the archwire into properly seated relation within the archwire slots defined by the other brackets of the lingual appliance.

BRIEF DESCRIPTION OF THE DRAWINGS

In order that the manner in which the above recited advantages and features of this invention are attained and can be understood in detail, more particular description of the invention briefly summarized above may be had by reference to the specific embodiments thereof that are illustrated in the appended drawings, which drawings form a part of this specification. It is to be understood, however, that the appended drawings illustrate only typical embodiments of the invention and are, therefore, not to be considered limiting of its scope, for the invention may admit to other equally effective embodiments.

IN THE DRAWINGS

Figure 1:
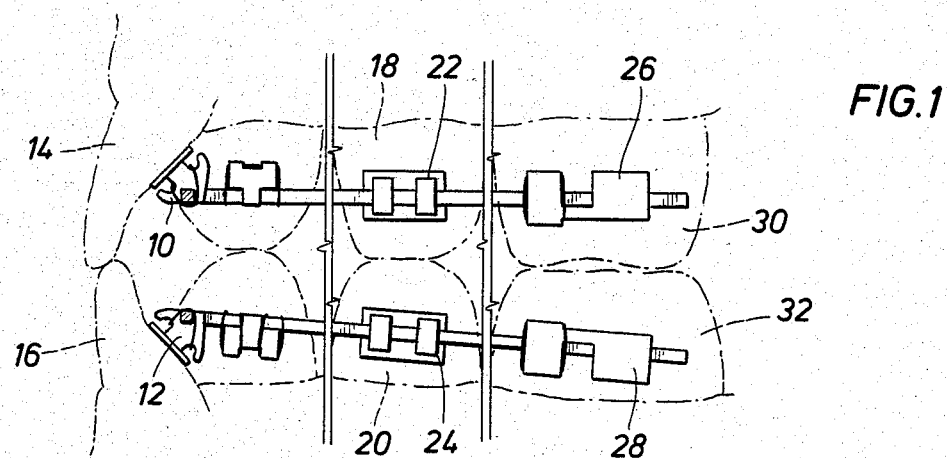

FIG. 1 is a pictoral representation of lingual orthodontic appliances which are attached to the teeth of an orthodontic patient.

Figure 2:
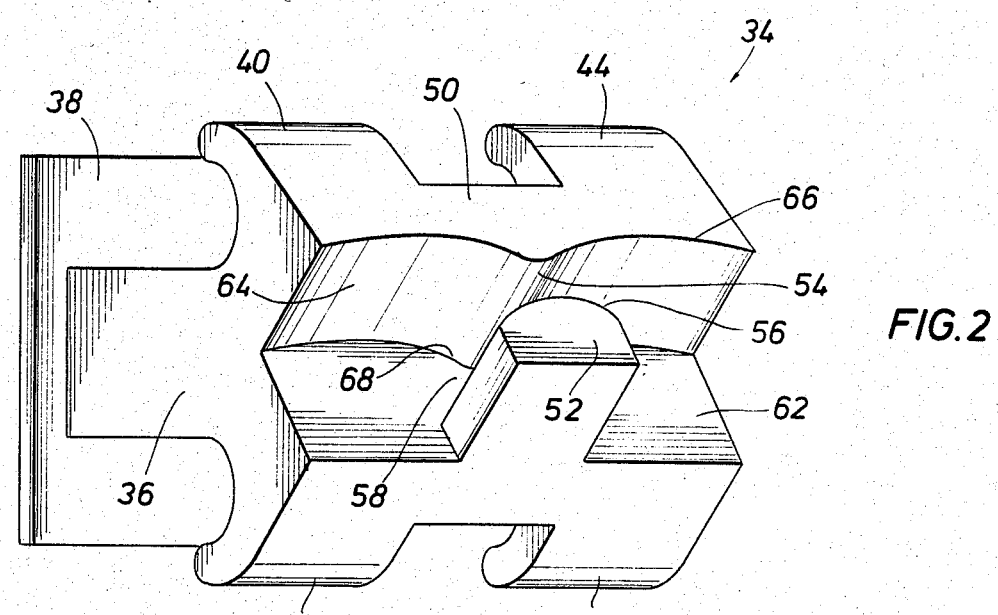

FIG. 2 is an isometric view of a twin lingual orthodontic bracket constructed in accordance with the present invention.

Figure 3:
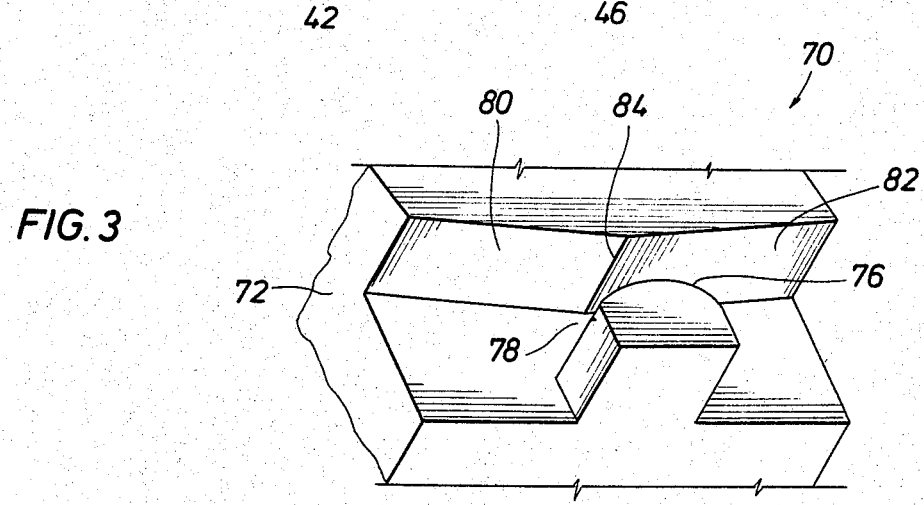

FIG. 3 is a fragmentary isometric view of a twin lingual bracket such as shown in FIG. 2 and which represents an alternative embodiment illustrating archwire relief by means of angulated surfaces extending from the active archwire slot.

Figure 4:
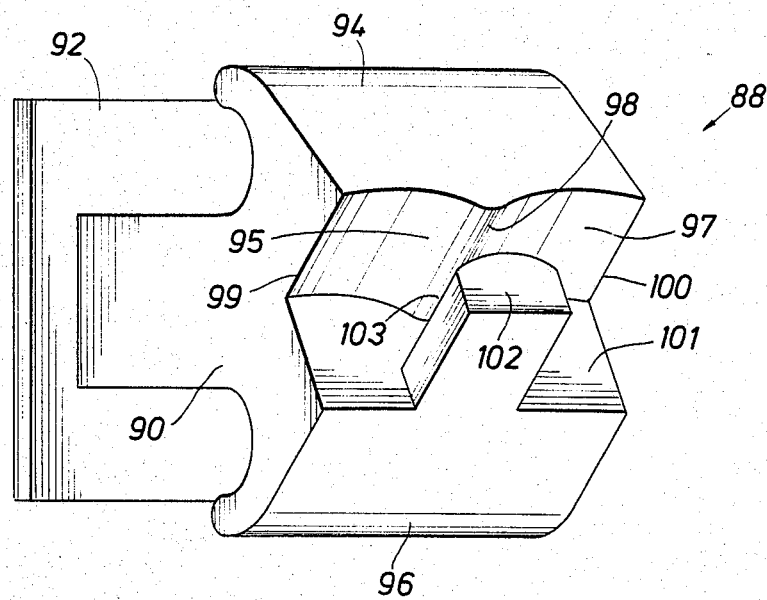

FIG. 4 is an isometric view illustrating a single tie wing type orthodontic bracket being configured for occlusal insertion of an archwire into the precision active archwire slot thereof.

Figure 5:
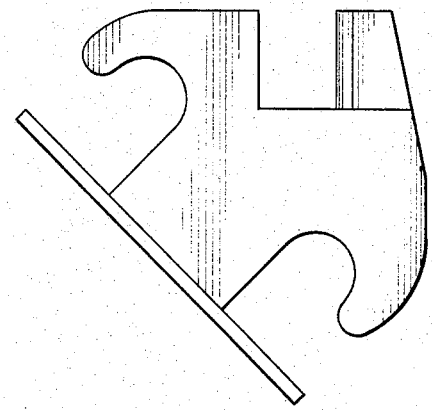

FIG. 5 is an end view of a single tie wing type lingual orthodontic bracket such as that shown in FIG. 4, which bracket is adapted for attachment to the anterior teeth of a patient.

Figure 6:
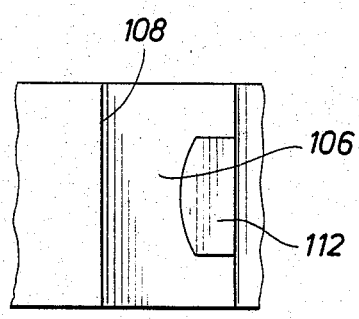

FIG. 6 is a fragmentary plan view of a bracket structure such as shown in FIGS. 4 and 5 and representing a further modified embodiment wherein the active archwire slot of the bracket structure is shown to be of arcuate configuration so as to receive the arcuate portion of an edgewise archwire.

Figure 7:
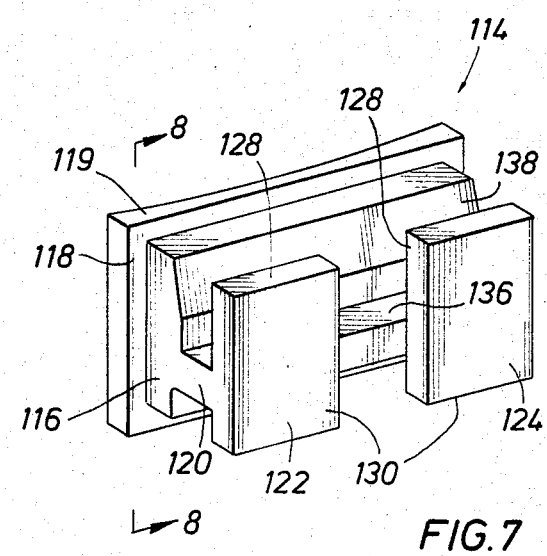

FIG. 7 is an isometric view of a lingual bicuspid bracket that is constructed in accordance with the present invention and is adapted for occlusal insertion of an archwire into the active archwire slot thereof.

Figure 8:
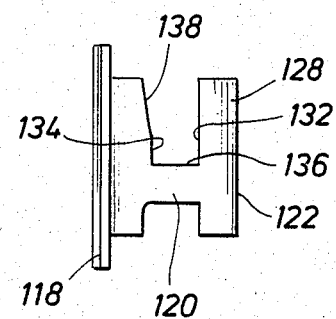

FIG. 8 is an end view of the lingual bicuspid bracket of FIG. 7.

Figure 9:
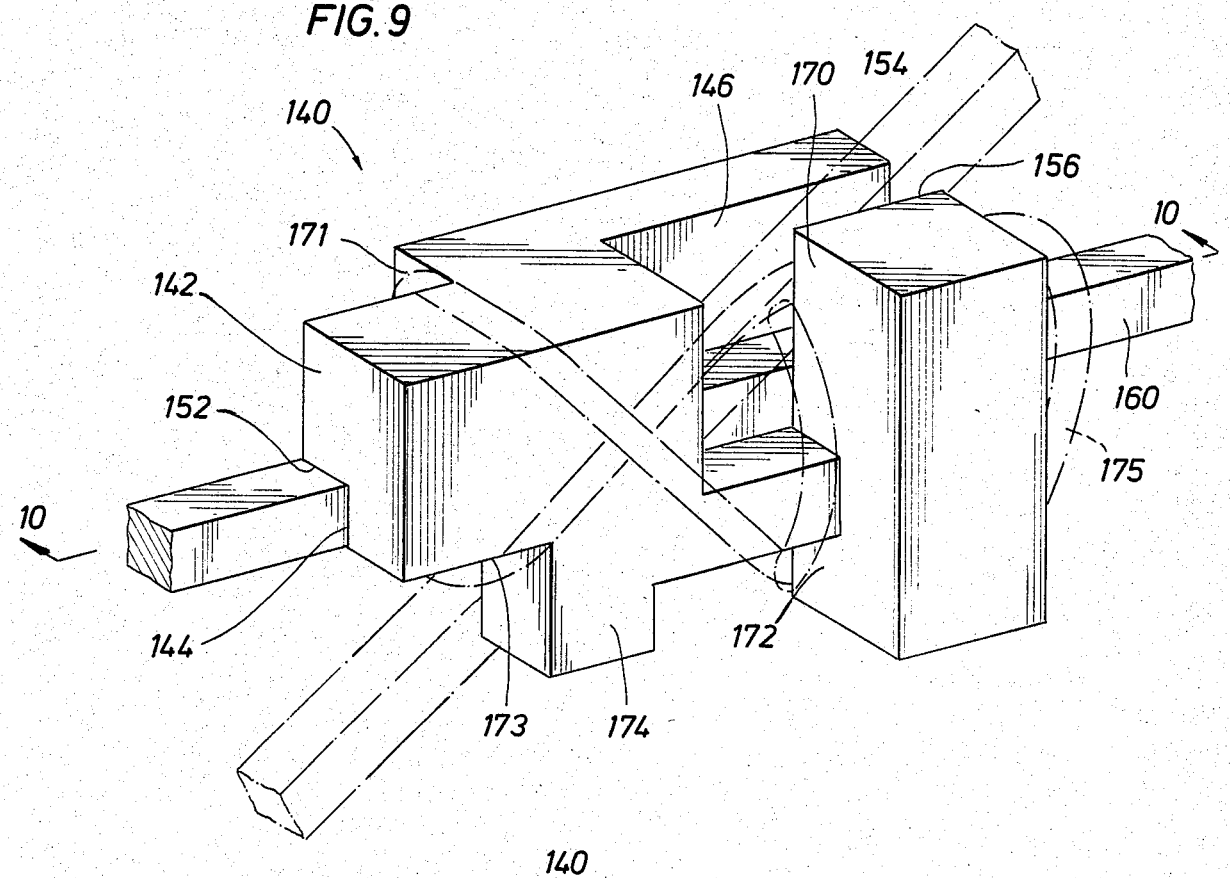

FIG. 9 is an isometric view illustrating a lingual tube such as constructed in accordance with the teachings of this invention and showing a portion of an archwire received therein in full line and further showing the angulated relation of an archwire in relation thereto during mesio-occlusal insertion of the archwire therein.

Figure 10:
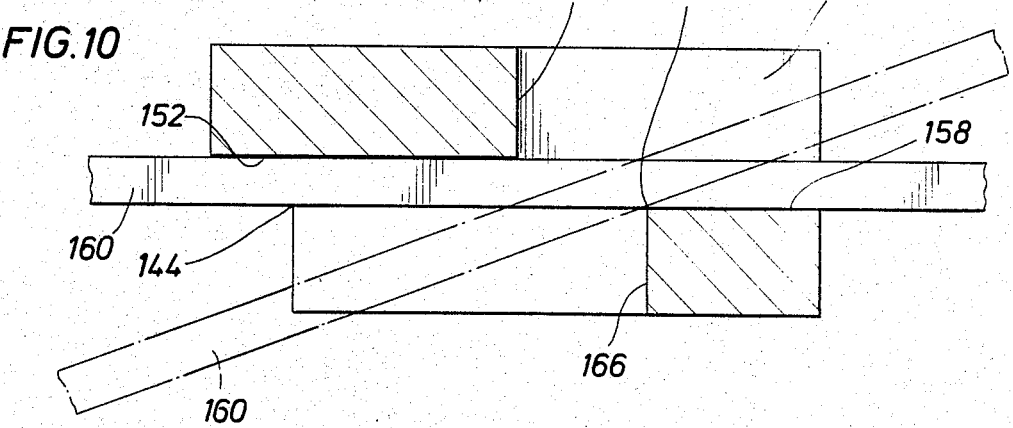

FIG. 10 is a sectional view taken along line 10—10 of FIG. 9 and illustrating in full line an edgewire archwire being received in operative relation therewith and further showing in broken line the angulated position of the archwire during mesio-occlusal insertion of the archwire therein.

Figure 11:
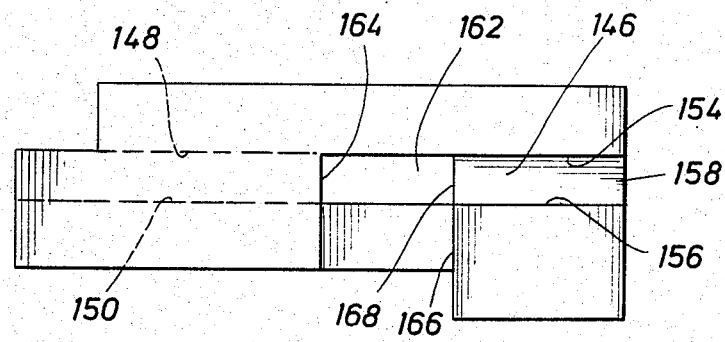

FIG. 11 is a plan view of the lingual tube bracket structure of FIG. 9.

FIG. 12 is an elevational view of a lingual bicuspid bracket representing a modified embodiment of this invention wherein the edgewise archwire is secured within the archwise slot of the bracket by means of a retainer pin.

FIG. 13 is a sectional view taken along line 13—13 of FIG. 12.

FIG. 14 is a sectional view of an interior lingual bracket illustrating pinned retention of the edgewise archwire.

FIG. 15 is a view of a lingual tube bracket for mesio-occulsal archwire insertion and illustrating pinned retention of an edgewise archwire.

FIG. 16 is a view toward the gingival of a lingual tube bracket representing a modified embodiment of the invention and illustrating an insertion slot for mesio-occlusal archwire insertion.

FIG. 17 is a sectional view of the bracket taken along line 17—17 of FIG. 16.

DETAILED DESCRIPTION OF PREFERRED EMBODIMENTS

Referring now to the drawings and first to FIG. 1, the fragmentary sectional pictoral illustration shows lingual portions of the maxillary and mandibular arches of a patient undergoing orthodontic therapy in accordance with the edgewise technique and incorporating a lingual orthodontic applicance system. As shown in FIG. 1, the various brackets of the lingual orthodontic system will be of differing construction, depending upon the characteristics of the teeth to which the brackets are to be applied. For example, at the left hand portion of FIG. 1, the brackets 10 and 12 of incisors 14 and 16 respectively will have the general configuration shown by the respective side views that are shown. For bicuspids such as shown at 18 and 20, lingual brackets will typically take another suitable form as shown at 22 and 24. At the respective ends of each of the maxillary and mandibular arches lingual tube orthodontic appliances such as shown at 26 and 28 are applied to respective molars 30 and 32 and will receive the respective end portions of the archwire 33 and 35. As will be explained in detail hereinbelow, the lingual tube brackets 26 and 28 are each adapted to receive the archwire extremities by mesio-occlusal insertion and provide the usual tube function as well as permitting occlusal insertion of the archwire into the archwire slots of other brackets of the orthodontic appliance system. The various orthodontic brackets of the lingual appliance system of FIG. 1 are explained in detail in FIGS. 2-11 hereinbelow.

Referring now to FIG. 2, a twin orthodontic bracket is shown generally at 34 which incorporates a bracket body structure 36 which may be of integral construction such as being formed of cast metal. The bracket body structure 36 incorporates a bonding pad 38 which is typically composed of metal and which is adapted to be bonded to the enamel lingual surface of a patient's teeth. The bonding pad 38 may be of any suitable configuration as is suitable to the bonding process and may be formed integrally with the bracket body structure 36 or attached to the bracket body by means of welding or by any other suitable form of attachment.

The bracket body is also formed to define pairs of tie wings such as shown at 40-42 and 44-46 which allow the archwire to be ligated to the bracket structure by means of ligature wire, ligature elastics or any other suitable means for securing the archwire to the bracket or applying force between the archwire and bracket.

It is desirable to provide a lingual orthodontic bracket for the edgewise technique that is basically in the form of a twin bracket structure which also incorporates over-rotational capability. In accordance with the present invention, the orthodontic bracket body 36 is formed to define an intermediate fulcrum section 50 which forms an intermediate projection 52. The intermediate fulcrum section 50 defines an intermediate fulcrum edge 54 which is positioned in spaced relation with an opposed curved fulcrum surface 56 that is defined by the projection 52. The fulcrum edge 54 and the curved fulcrum surface 56 cooperate to define a precision active archwire slot which is adapted to receive the respective edgewise archwire 33-35 in close fitting relation therewith. Although edgewise archwires for finishing activities are of rectangular cross-sectional configuration, it should be borne in mind that edgewise archwires for accomplishing tooth movement in the initial stages of orthodontic therapy are defined by wires having a round cross-sectional configuration. The archwire slot is completed by a bottom wall or surface 58 which is contiguous with flat surfaces 60 and 62 and which faces toward the occlusal. In fact, the flat surfaces 60 and 62, together with the bottom wall surface 68 of the active archwire slot can be said to be defined by a single flat surface. It is not necessary, however, that surfaces 60 and 62 be of flat configuration except that these surfaces should have no interference with the relationship of the archwire to the bottom wall surface 58 of the archwire slot.

The intermediate fulcrum section 50 provides for rotation of the bracket and tooth in relation to the archwire. To provide the bracket with this rotational capability, it is necessary that the bracket structure provide archwire relief on either side of the fulcrum section. To accomplish these purposes, the bracket body 36 is formed to define concave, curved relief surfaces 64 and 66 which are positioned in recessed relation with respect to the fulcrum edge 54 of the archwire slot. It is desirable that the surfaces 64 and 66 be sufficiently relieved in relation to the archwire that these surfaces do not come into contact with the archwire even under circumstances were the archwire is in angulated relation with the archwire slot at the tie wing portions of the bracket structure. Although it is preferable that the archwire not come into contact with the relieved surfaces 64 and 66, it should be borne in mind that during the early stages of orthodontic treatment, especially in cases of gross malocclusion, the archwire may require sufficient bending that it comes into contact with another edge 65 or 67 defined by one of the archwire relief surfaces at the respective side portion of the bracket. Logically, interbracket width is then limited. As soon as the maloccluded teeth being to move in response to therapy, however, the outer edge 65 or 67 of the bracket will move out of contact with the archwire. As soon as this occurs, maximum interbracket width will be established and, from that point or further tooth movement will occur in response to the total interbracket width between adjacent fulcrum sections. The archwire may, therefore, be ligated with either one of the pairs of tie wings of the bracket in such manner that the archwire provides bracket and tooth rotational capability as the archwire tends to return to its normal configuration and thus imparts a rotational force through the bracket to the tooth. Further, the intermediate fulcrum section of the bracket and the relieved portions of the bracket structure in the tie wing areas cooperate to define a bracket structure having greater interbracket width than is ordinarily afforded by twin orthodontic brackets. In fact, assuming the active archwire slot of the bracket structure of FIG. 2 to be the same or less width as compared to the length of the archwire slot of a conventional single orthodontic bracket, the twin lingual bracket of FIG. 2, therefore, defines an interbracket width that is at least as great as the interbracket width defined by conventional single orthodontic brackets. As mentioned above, the length of the archwire span that exists between adjacent single orthodontic brackets allows lower magnitude forces to be applied to the teeth over longer periods of time as compared to circumstances where the interbracket width is limited and the archwire span is short, such as is typical in the case of adjacent twin brackets of conventional nature. By providing the twin bracket of FIG. 2 with an intermediate fulcrum section and with relieved areas between the pairs of tie wings, the free archwire between the adjacent fulcrum sections of adjacent brackets will be as long as ordinarily possible to edgewise orthodontic therapy. The long span of archwire may, therefore, be twisted much further without causing permanent yielding or deformation of the metal from which the archwire is formed. In returning or springing back to its normal configuration, the edgewise archwire will, therefore, apply a tooth moving force to the tooth over a longer period of time, as compared to conventional twin brackets, without adjustment of the orthodontic appliance. This feature, of course, minimizes the frequency of adjustment of the orthodontic appliance and thus significantly minimizes the amount of chair time and the frequency of visits that are required during the period of orthodontic therapy.

The intermediate fulcrum section of the bracket structure, together with the relieved tie wing portions of the bracket, provide efficient over-rotational control, thus allowing the orthodontist to move the teeth rapidly to the final positions thereof and minimizing the treatment time necessary for effecting movement of the teeth to proper occlusion within the alveolar arch.

FIG. 3 is a fragmentary isometric view illustrating a bracket structure similar to that of FIG. 2, wherein the archwire relief is defined by angulated surfaces 80 and 82 diverging from a central fulcrum edge 84. As shown in FIG. 3, the alternative embodiment illustrated generally at 70 incorporates a bracket body structure 72 forming twin tie wing areas similar to that of FIG. 2 and forming an intermediate fulcrum section having an active archwire slot that is defined by a vertical fulcrum edge 74 and a curved fulcrum surface 76, together with a bottom surface 78. Desired archwire relief for over-rotational control and maximizing interbracket width is defined by a pair of angulated relief surfaces 80 and 82 that extend from the fulcrum edge 84. The fulcrum edge 84 cooperates with the curved fulcrum surface 76 to define line contact on each side of the archwire. This parallel line contract establishes opposed lines of active archwire reaction and defines interbracket width of maximum span. Any bending or twisting of the archwire between adjacent brackets extends from the line contact with fulcrum edge 84 and line con act with curved fulcrum surface 76. The function of the orthodontic bracket of FIG. 3 is essentially the same as that described above in connection with FIG. 2.

It may be desirable to provide a lingual type single orthodontic bracket under circumstances where size makes twin tie wings impractical. In such case, the bracket structure may conveniently take the form illustrated in FIG. 4 where a single lingual orthodontic bracket is shown generally at 88. The orthodontic bracket 88 incorporates a bracket body structure 90 to which is interconnected or integrally formed a bonding base 92 for bonding of the bracket to the lingual surfaces of the teeth of a patient undergoing orthodontic therapy.

The bracket body is formed to define a single pair of opposed tie wings 94 and 96 which enable the archwire to be ligated to the bracket structure with ligature wire, ligature elastics or other suitable means of ligation. The body structure 90 is also formed to define a pair of curved relief surfaces 95 and 97 which are positioned on opposed sides of a centrally oriented fulcrum edge 98 extending to outer edges 99 and 100. A planar surface 101 is also formed by the bracket body which also establishes the bottom wall of the active archwire slot. A projection 102 extends from the body structure 90 opposite the fulcrum edge 98 and forms a curved fulcrum surface 103. Projection 102 is positioned between the opposed tie wings 94 and 96 so that a ligature wire or elastic looped around the tie wings will also be looped around the intermediate projection 102 to thus secured the archwire to the bracket structure in close proximity to the projection 102. The projection 102 is formed integrally with the bracket body structure 90 and presents the curved fulcrum surface 103 in parallel oriented relation with the opposite fulcrum edge 98. The opposed fulcrum edge 98 and curved fulcrum surface 103 cooperate to define a precision archwire slot 104 within with an edgewise archwire is received in active relation therewith. That portion of planar surface 101 that extends between the opposed fulcrum edge 98 and curved fulcrum surface 103 also functions to define the bottom wall of the precision archwire slot. The flat sided edgewise archwire will have line contact with the fulcrum edge 98 and curved fulcrum projection surface 103.

The projection 102 functions as an integral part fulcrum portion of the bracket structure thus providing a pivot area intermediate the extremities of the bracket. Further, the projection 102, being relieved at each extremity thereof, allows the archwire to have a maximum interbracket width with respect to the intermediate projection or fulcrum of the adjacent orthodontic bracket.

Since the archwire of the lingual orthodontic appliance system will have an arched or curved portion having less radius of curvature as compared to conventional labial orthodontic appliances, it may be necessary to provide the various active archwire slots of the brackets with the capability of receiving the curved archwire in active engagement therewith. As shown in FIG. 6, brackets according to this invention may be provided having a precision archwire slot such as shown at 106 which is at least partially defined by a generally planar surface 108 and an opposed convex surface 110 that are cooperatel formed by the body portion of the bracket structure. As shown, planar surface 108 is formed by the body of the bracket while the convex surface 110 is formed by an intermediate projection 112 extending from the body. Otherwise, the bracket structure shown in FIG. 6 may be quite similar to the bracket structure of FIG. 5 or may conform to the bracket structures of FIGS. 2 and 3. Obviously, only those orthodontic brackets that are located on anterior teeth would be provided with active archwire slots of curved configuration because the brackets of bicuspids and molars ordinarily receive relatively straight portions of the edgewise archwire.

In accordance with the lingual edgewise technique of this invention, orthodontic brackets for bicuspids and molars must have a configuration substantially differing from the configuration of brackets for anterior teeth. As shown in FIGS. 8 and 9, a lingual bracket for the edgewise technique may conveniently take the form illustrated generally at 114. The lingual bicuspid bracket may incorporate a bracket body structure 116 of generally rectangular form having a bonding pad 118 extending therefrom. The bonding pad will ordinarily be composed of metal and may be formed integrally with the bracket body 116 or, in the alternative, may be connected to the bracket body in any suitable manner such as by welding, bonding, etc. If desired, the bonding pad 118 may be composed of any suitable material other than metal for attachment of the bracket to the lingual surface of a bicuspid or molar. The bonding pad defines a curved bonding surface 119 that corresponds to the curvature of the lingual surface of the bicuspid.

The body structure 116 of the bracket is formed to define an intermediate shelf 120 which extends laterally from the intermediate portion of the bracket body and is oriented in generally parallel relation with the occlusal. Although the intermediate shelf may be of generally rectangular configuration, it may also be of the configuration shown in FIG. 8 where the shelf defines spaced projecting tie wing retainer portions 122 and 124. These tie wing retainer portions are provided to facilitate retention of the archwire in proper relation with the shelf and with the archwire slot. The tie wing retainer projections of the bracket structure each define upper and lower tie wing projections 128 and 130 that extend respectively beyond the horizontal surfaces of the shelf 120. The upper portion 128 of each of the tie wings 122 and 124 each defines an inner planar surface 132 as shown in FIG. 8 that is positioned in parallel, spaced relation with a planar surface 134 defined by the bracket body 116 thus forming an active archwire slot to receive the edgewise archwire. The planar surface 136 of the shelf 120 cooperates with parallel surfaces 132 and 134 to define the bottom wall or surface of the active archwire slot. The bracket structure 113 is also formed to define an angulated, generally planar surface 138 which functions as a guide surface to permit efficient entry of the edgewise archwire into its active relationship with the archwire slot defined by surfaces 132-134-136. The angulated planar surface 138 also provides relief to thus enable efficient ligating of the archwire in respect to the tie wing portion of the bracket structure. It should be borne in mind that the archwire slot of the bracket 114 is readily adapted to allow occlusal insertion of the archwire therein. This feature effectively facilitates efficient handling of the archwire during installation thereof. Further, for maloccluded teeth, simple force application to the archwire will enable it to be guided by surface 138 into the active archwire slot, thus appropriately bending or twisting the archwire to allow archwire developed force application to the bracket and tooth.

In accordance with edgewise orthodontic therapy, the opposed end portions of each archwire are typically received by molar tubes. In order to allow occlusal insertion of the archwire into the active archwire slots of the respective brackets of the lingual orthodontic appliance system, it is desirable to provide a lingual type tube bracket having the capability of receiving the extremities of the archwire in accordance with typical tube function and yet having the capability of permitting mesio-occlusal insertion of the archwire therein to permit occlusal insertion of the archwire into the archwire slots of the remaining brackets. In accordance with the present invention, a lingual tube bracket may conveniently take the form illustrated in FIGS. 9-11. As shown in the isometric view of FIG. 9, the lingual tube bracket is illustrated generally at 140 and incorporates a body structure 142 defining an archwire slot portion 144 at one extremity of the bracket which opens toward the gingival while at the opposite extremity of the bracket, an archwire slot portion 146 is defined which opens toward the occlusal. The archwire slot portion 144 is defined by parallel intermediate bracket surfaces 148 and 150 shown in broken line in FIG. 11 and a transverse planar surface 152 that intersects surfaces 148 and 150 in normal relation. Thus, surfaces 148, 150 and 152 cooperate to define rectangular archwire slot portion 144.

The archwire slot portion 146 is defined by parallel surfaces 154 and 156 which are disposed in parallel relation and a transverse surface 158 which intersects surfaces 153 and 156 in normal relation. The pairs of parallel surface 148-150 and 154-156 are each formed by precision machining or molding such that the archwire 160 is received in active relation within the respective archwire slot portions 144 and 146.

As mentioned above, it is desirable that the archwire 160 have the capability of being inserted into assembly with the lingual tube bracket structure 140 by means of mesio-occlusal insertion. This feature is shown in full lines and broken lines in FIGS. 9 and 10. To permit mesio-occlusal insertion of the archwire, the lingual tube bracket is formed to define an opening 162 which extends completely through the bracket structure. This opening is defined in part by surfaces 164 and 166 which are identified more clearly in the sectional view of FIG. 10 and the plan view of FIG. 11. The edge 168 defined by intersecting surfaces 158 and 166 functions as a pivot, about which the archwire 160 is enabled to rotate as it is moved from the inclined, broken line position shown in FIG. 10 to the normal, operative position shown in full line in FIGS. 9 and 10. The extremities of the archwire 160 are thus inserted mesio-occlusally through the openings 162 of the lingual tubes and, after being so positioned, the archwire is then rotated about the edge 168 to the full line position shown in FIGS. 9 and 10. Upon reaching the full line position, the remaining portions of the archwire are inserted occlusally into the respective active archwire slots of the other brackets of the lingual orthodontic appliance. When the archwire 160 is in contact with the tube defining surfaces 152 and 158 of the lingual tube, it functions in the same manner as if the lingual tube were provided with a single elongated rectangular opening. The archwire is then ligated with respect to the lingual tube by means of ligature wires or elastics which extend about opposed tie wing portions 170 and 172 of the bracket structure. The body structure of the bracket is cut away at 171 and 173 forming corners or notches that adapt the bracket to receive ligating devices such as wires, elastic members, etc., as shown in broken line. As shown in broken line, the tie wings 170 and 172 may be in registry with the outer wall surface 174 of the bracket structure or, as shown in full line, may extend outwardly beyond the wall surface to facilitate ease of ligation. Ligating devices such as wires, elastic bands, etc., may also be looped around the tie wings 170 and 172 as shown in broken line at 175.

A lingual orthodontic bracket system has been shown in FIGS. 1-11 wherein an edgewise archwire may be inserted mesio-occusally into the archwire slots of the interrelated bracket system and may then be ligated to the brackets by means of ligature wire, elastic bands, etc. It may be desirable to secure the edgewise archwire in assembly within the active archwire slots of the brackets by means other than a ligating system. In accordance with the features of this invention, such bracket structure may conveniently take the form set forth in FIGS. 12-14. FIGS. 12 and 13 relate to lingual orthodontic bracket structures which are received by the bicuspids of the patient while FIG. 14 shows a lingual orthodontic bracket for anterior teeth. In each case, the archwire is secured to the bracket structure by means of a retainer pin similar to that utilized in conjunction with the Begg light-wire technique.

Referring now to FIGS. 12 and 13, a lingual orthodontic bracket is shown generally at 180 which incorporates a bonding base 182 having a bonding surface which is contoured for close fitting relation with the lingual surface of the bicuspid. A bracket body structure 184 extends from the bonding base and defines a projecting support shelf 186 which extends the width of the body. Tie wing projections 188 and 190 extend from respective extremities of the support shelf 186 and define upper and lower tie wings that receive ligating devices to secure an edgewise archwire in assembly with the bracket structure. As shown, the tie wing projection 188 defines tie wing portions 190 and 192 while tie wing projection 190 defines tie wing extensions 194 and 196. In this manner, the lingual bracket 180 is similar to the bracket construction illustrated in FIG. 7.

In order to provide for pinned retention of the edgewise archwire in assembly with the bracket, an intermediate projection 198 extends from the central portin of the support shelf 186. The intermediate projection 198 defines a bore or passage 200 through which is extended the shaft portion 202 of a retainer pin 204. The retainer pin includes a transverse retainer head portion 206 which overlies the edgewise archwire 208 which is received within the active archwire slot portions defined at each extremity of the bracket structure in the manner discussed above in connection with FIG. 7. The elongated shaft portion 202 of the retainer pin extends well beyond one extremity of the intermediate projection 198 and may be bent over as shown in FIG. 12, thus locking the retainer pin in connection with the intermediate projection. In this manner, the archwire may be secured in assembly with the bracket structure without necessitating the use of ligating devices. Also, if desired, ligating devices may be employed on one or the other of the tie wing projections 188 or 190 as desired for accomplishing tooth movement in accordance with the edgewise technique. The pin 204 is removed by straightening the lower extremity and then extracting it from the bore 200.

A pin retention type orthodontic bracket for the anterior teeth is shown generally at 210 in FIG. 14. The bracket 210 incorporates a bonding base 212 for bonding of the bracket structure to the lingual surface of a patient's tooth. The bracket also incorporates a body structure 214 which defines an archwire slot 216 in the same manner as discussed above in connection with FIGS. 4 and 5, for example. The intermediate fulcrum portion of the bracket structure is formed to define a pin receptacle or projection portion 218 which defines a bore or passage 220 within which is received the elongated shaft or shank portion 224 of a retainer pin 226. The retainer pin also defines a transverse retainer head portion 228 which overlies the archwire slot 216 and functions to secure an edgewise archwire in active relation therein. The elongated shaft or shank 224 of the pin extends well beyond one extremity of the projection 218 and may be bent over in the same manner as shown in FIG. 12 in order to secure the pin in locked relation within the bore or passage 222.

The retainer pins 204 and 226 of FIGS. 13 and 14 respectively may be composed of any suitable malleable metal or other material which may be bent over to secure the pin in place and may be straightened without breaking although the bracket structure shown in FIGS. 12–14 incorporate a Begg-type retainer pin, nevertheless, these brackets incorporate the edgewise technique and are not to be confused with the light-wire technique of Begg.

It may also be desirable to secure an archwire in assembly with a lingual tube bracket by pinning rather than by ligation as in the case with the lingual tube bracket of FIG. 9. In order to accomplish this featuer, a modified lingual tube bracket may be provided in the manner illustrated generally at 230 in FIG. 15. The lingual tube bracket 230 incorporates a body structure 232 which forms an elongated active archwire groove 234 in the same manner as discussed above in connection with FIG. 9. The archwire groove or slot 234 is of generally rectangular form and has an active relationship with the flat surfaces of the rectangular edgewise archwire 236. The body structure 232 is formed to define a retainer projection 238 having an elongated passage 240 extending therethrough. A retainer pin 242 forming an elongated shank 243 is adapted to be extended through the passage 240 in such manner that a terminal portion of the shank extends beyond the retainer portion 238 of the bracket. The retainer pin 242 is formed at one extremity to define an enlarged retainer head 244 which is offset relative to the shank portion of the retainer pin. A portion of the enlarged head is adapted to overlie and engage the upper portion of the archwire 236 thereby positively securing it in active relation within the archwire slot 234.

For mesio-occlusal insertion of an edgewise archwire into the active archwire slot of a lingual tube bracket, the bracket structure may take the form shown generally at 250 in FIGS. 16 and 17. FIG. 16 is a view toward the gingival while FIG. 17 is a sectional view taken along line 17—17 of FIG. 16 and viewing toward the lingual. As shown in FIG. 16, the lingual tube bracket structure 250 comprises a bracket body structure 252 having a bonding base 251 extending therefrom. The bonding base defines an arcuate bonding surface conforming to the curvature of the molar to which the bracket is to be bonded. The body structure 252 of the bracket defines an elongated active archwire slot 254 formed in part by upper and lower surfaces 256 and 258 and by planar surfaces 262 and 264. An edgewise archwire 268 is received in active relation within the archwire slot 254.

To facilitate insertion of the free extremities of the edgewise archwire 268, the body structure 252 of the bracket is formed to define an entry groove 266 which is formed in part by an angulated guide surface 260 and by extended portions of the planar surfaces 262 and 264. As shown in broken line in FIG. 17, the archwire 268 is positioned in angulated relation with the archwire slot 254 and is inserted mesio-occlusally into the archwire slot. The angulated guide surface 250 guides the free extremities of the archwire from the entry slot 266 into active relation within the archwire slot. Although the archwire 268 may be quite stiff, such as during finishing therapy, it nevertheless is flexible to some degree. After the free extremities of the archwire have been inserted into the entry slot 266 and are fed into the beginning portion of the archwire slot 254, the archwire may be flexed to some extent toward the gingival. Flexing of the free extremities causes the end portions of the archwire to become oriented in substantially parallel relation with respect to the active archwire slot 254. By simply applying a force to the archwire, the free extremities of the archwire will be guided into and along the archwire slot. The angular relationship of the archwire during such mesio-occlusal insertion movement is quite small since the curved portion of the archwire need only clear the anterior teeth before the archwire is pivoted to move the curved portion into the active archwire slots of the anterior bicuspid and molar teeth.

In comparing the lingual tube bracket structures of FIGS. 16 and 17 with that of FIGS. 9–11, it is clear that the archwire need not be extended completely through the bracket structure of FIGS. 16 and 17 to accomplish mesio-occlusal insertion of the archwire into the active slots of the respective brackets.

In view of the foregoing, it is apparent that I have provided a lingual orthodontic appliance system which may be effectively utilized in accordance with the edgewise technique for efficient orthodontic therapy. Orthodontic therapy may be readily conducted while at the same time, the labial and buccal surfaces of the teeth of the patient remain clear of obstructions so that efficient cleaning may be readily conducted and oral hygiene more easily maintained. Moreover, the outward appearance of the teeth of the patient will be quite pleasant and the patient will not, therefor, be subjected to the degree of psychological trauma ordinarily associated with application of orthodontic appliances to the labial surfaces of the teeth.

The lingual orthodontic appliances of the present invention are designed such that the edgewise archwire is adapted to be inserted into the respective active archwire slots by means of occlusal insertion. This feature effectively facilitates ease of installation of the archwire and ease of adjustments that are typically made during orthodontic therapy.

The various orthodontic appliances of this lingual system shall employ a fulcrum controlled twin tie wing technique where appropriate for accomplishment of efficient rotation which is ordinarily beyond the capability of twin orthodontic appliances in conjunction with the edgewise technique. The lingual orthodontic appliance system of this invention also incorporates molar tubes which allow mesio-occlusal insertion of the archwire therein and which provides a typical tube bracket function when the archwire is in operative relation therewith. The bracket structures may be designed for ligature or pin retention of the edgewise archwire as desired. It is, therefore, apparent that the present invention is one adapted to attain all of the objects and features hereinabove set forth, together with other features which are inherent in the description of the apparatus itself.

While the foregoing is directed to the preferred embodiments of the present invention, other and further embodiments of the invention may be devised without departing from the basic concept thereof, and the scope of this invention is determined by the claims which follow.

I claim:

1. A lingual orthodontic bracket for edgewise orthodontic therapy of teeth in the maxillary and mandibular arches, comprising:
   (a) base means adapted for attachment to the lingual surface of a tooth and defining proximal edges;
   (b) spaced pairs of ligating tie wing means extending from said base means;
   (c) a central bracket section being formed by said base means between said proximal edges and intermediate said spaced pairs of tie wing means and defining first archwire reaction surface means, projection means extending from said central bracket section and defining second archwire reaction surface means being parallel with said first archwire reaction surface means and cooperating therewith to define precision edgewise archwire slot means opening toward the occlusal and oriented for occlusal and mesial insertion of an edgewise archwire therein; and
   (d) said base means defining archwire relief at each side of said archwire slot means permitting bracket-/archwire engagement only at said archwire slot means of said central bracket section, whereby interbracket width between adjacent similar brackets is greater than the spacing of the base means thereof.

2. A lingual orthodontic bracket as recited in claim 1, wherein said edgewise archwire is of rectangular cross-sectional configuration defining parallel labial and lingual surfaces and parallel occlusal and gingival surfaces, and:
   said labial and lingual surfaces of said archwire are received in force transmitting engagement by said parallel opposed first and second archwire reaction surface means to control torque by interaction with said labial and lingual surfaces of the edgewise archwire.

3. A lingual orthodontic bracket as recited in claim 1, wherein said ligating tie wing means comprises:
   (a) pairs of twin tie wings located at respective mesial and distal extremities of said base means said pairs of twin tie wings being oriented in spaced relation; and
   (b) said parallel archwire reaction surface means of said central bracket section and said projection means are of curved configuration defining opposed fulcrum surfaces located at least partially between said spaced pairs of tie wings, said curved fulcrum surfaces being parallel with one another and precision spaced to receive the labial and lingual surfaces of said edgewise archwire in mechanically interactive relation therebetween according to edgewise orthodontic therapy.

4. A lingual orthodontic bracket as recited in claim 1, wherein said ligating tie wing means comprises:
   (a) first tie wing means extending from said base means on the labial side of said archwire slot;
   (b) second tie wing means extending from said base means on the lingual side of said archwire slot; and
   (c) said central bracket section being located between said first and second tie wing means.

5. A lingual orthodontic bracket as recited in claim 1, wherein:
   said archwire relief extends from the area of contact between said archwire and said first and second archwire reaction surface means forming said archwire slot means to respective extremities of said base means, said archwire relief being both labial and lingual relief to permit controlled rotational movement of the tooth to which the bracket is secured in sole response to mechanical interaction between said archwire and said archwire slot means of said central bracket section.

6. A lingual orthodontic bracket as recited in claim 5, wherein:
   said archwire relief is defined in part by lingually diverging inclined surfaces extending from said archwire slot means to respective proximal edges of said base means.

7. A lingual orthodontic bracket as recited in claim 5, wherein:
   said archwire relief is defined by recesses formed by said base means and extending from said archwire slot means to respective proximal edges of said base means.

8. A lingual orthodontic bracket as recited in claim 1, wherein:
   (a) said central bracket section forms said first archwire reaction surface means; and
   (b) said projection means extends from said central bracket section of said base means, said projection means forming said second archwire reaction surface means positioned in spaced parallel relation with said first archwire reaction surface means, said projection means being positioned intermediate the extremities of said base means and cooperating with said base means to form at least a portion of said archwire relief means.

9. A lingual orthodontic bracket as recited in claim 8, wherein:
   (a) said first archwire reaction surface means is an intermediate edge formed by said central bracket section of said base means and adapted for active engagement by said archwire; and
   (b) said second archwire reaction surface means is a partially cylindrical surface being defined by said projection means and being parallel with said first archwire reaction surface means of said central bracket section of said base means and spaced sufficiently therefrom to permit active engagement with said archwire in accordance with edgewise orthodontic therapy, said first archwire reaction surface means and said second archwire reaction surface means cooperating to form said archwire slot means.

10. A lingual orthodontic bracket for edgewise orthodontic therapy of teeth in the maxilliary and mandibular arches, comprising:

(a) base means adapted for attachment to the lingual surface of a tooth and defining proximal edges;

(b) a central bracket section being formed by said base means between said proximal edges, said central bracket section defining central archwire reaction surface means of less width than said base means and archwire relief surfaces extending from each side of said central archwire reaction surface means and terminating at respective proximal edges of said base means;

(c) bottom surface means being formed by said central bracket section of said base means and being oriented in substantially normal relation with the occlusal;

(d) projection means extending from said central bracket section and defining second archwire reaction surface means oriented in spaced parallel relation with said central archwire reaction surface means and in substantially normal relation with said bottom surface means, said central archwire reaction surface means, said bottom surface means and said second archwire reaction surface means cooperating to define precision edgewise archwire slot means of less proximal to proximal width as compared to that of said base means and opening toward the occlusal for occlusal and mesial insertion of an edgewise archwire therein, said parallel central archwire reaction surface means and said second archwire reaction surface means being operative to receive the labial and lingual surfaces of an edgewise archwire in mechanically interactive relation therebetween according to edgewise orthodontic therapy, whereby rotational tooth movement is accomplished solely in response to said mechanically interactive relation between said archwire and said central archwire reaction surface means and said second archwire reaction surface means and interbracket width between adjacent similar brackets is greater than the spacing of the base means thereof.

11. A lingual orthodontic bracket as recited in claim 10, wherein:

said central archwire reaction surface means and said second archwire reaction surface means are of partially cylindrical configuration and define opposed lines of contact with said edgewise archwire.

12. A lingual orthodontic bracket as recited in claim 10, wherein:

(a) said central archwire reaction surface means is defined by converging surface means; and (b) said second archwire reaction surface means is of partially cylindrical configuration defining line contact with said edgewise archwire.

13. A lingual orthodontic bracket as recited in claim 12, wherein:

said converging surface means are of planar configuration defining a central archwire reaction edge disposed for line contact with said edgewise archwire.

14. A lingual orthodontic bracket as recited in claim 10, wherein:

said central archwire reaction surface means is of planar configuration and is disposed for surface-to-surface engagement with said edgewise archwire.

15. A lingual orthodontic bracket as recited in claim 10, wherein:

said bottom surface means extends from said central bracket section to the respective proximal edges of said base means and also extends from said projection means to the respective proximal edges of said base means.

* * * * *